US011505774B2

(12) United States Patent
Makino et al.

(10) Patent No.: US 11,505,774 B2
(45) Date of Patent: Nov. 22, 2022

(54) SAMPLE STORAGE APPARATUS

(71) Applicants: NIHON KOHDEN CORPORATION, Tokyo (JP); OSAKA UNIVERSITY, Suita (JP)

(72) Inventors: Hodaka Makino, Tokorozawa (JP); Hirotsugu Kubo, Tokorozawa (JP); Tetsuya Ogawa, Tokorozawa (JP); Masahiro Kinooka, Suita (JP)

(73) Assignees: NIHON KOHDEN CORPORATION, Tokyo (JP); OSAKA UNIVERSITY, Osaka (JP)

( * ) Notice: Subject to any disclaimer, the term of this patent is extended or adjusted under 35 U.S.C. 154(b) by 117 days.

(21) Appl. No.: 16/659,825

(22) Filed: Oct. 22, 2019

(65) Prior Publication Data
US 2020/0123489 A1   Apr. 23, 2020

(30) Foreign Application Priority Data

Oct. 23, 2018   (JP) .............................. JP2018-199369

(51) Int. Cl.
*C12M 1/00* (2006.01)
*C12M 1/34* (2006.01)
*C12M 1/12* (2006.01)

(52) U.S. Cl.
CPC ............ *C12M 23/38* (2013.01); *C12M 29/00* (2013.01); *C12M 37/00* (2013.01); *C12M 41/00* (2013.01)

(58) Field of Classification Search
CPC ....... C12M 29/00; C12M 23/40; C12M 29/10
See application file for complete search history.

(56) References Cited

U.S. PATENT DOCUMENTS

| | | | | |
|---|---|---|---|---|
| 3,647,633 A | * | 3/1972 | Dawson | C12M 29/10 435/286.7 |
| 4,997,660 A | * | 3/1991 | Wittier | B01D 19/02 426/17 |
| 5,089,385 A | * | 2/1992 | Kiel | C12M 29/10 435/173.1 |
| 5,811,259 A | * | 9/1998 | Hall | C12M 23/34 210/903 |
| 6,797,508 B1 | * | 9/2004 | Holker | C02F 11/02 435/252.1 |
| 2009/0078124 A1 | * | 3/2009 | Vason | C12M 45/03 99/278 |
| 2009/0176301 A1 | * | 7/2009 | Oldenburg | C12M 27/02 435/297.1 |
| 2010/0047889 A1 | * | 2/2010 | Davis | C12M 21/12 435/162 |

(Continued)

FOREIGN PATENT DOCUMENTS

JP    2012-200239 A    10/2012

*Primary Examiner* — Holly Kipouros
(74) *Attorney, Agent, or Firm* — Sughrue Mion, PLLC

(57) ABSTRACT

A sample storage apparatus includes: a lid member; a sample storage container; first and second fluid sucking sections; first and second fluid discharging sections; first to fourth flow paths; and a first fluid identification sensor. The first flow path is connected to the first fluid sucking section, the second flow path is connected to the second fluid sucking section, the third flow path is connected to the first fluid discharging section, and the fourth flow path is connected to the second fluid discharging section. The first fluid identification sensor for identifying a fluid is disposed in the first flow path.

22 Claims, 12 Drawing Sheets

(56) References Cited

U.S. PATENT DOCUMENTS

| | | | | |
|---|---|---|---|---|
| 2011/0111497 A1* | 5/2011 | Tamai | ................... | C12M 47/02 |
| | | | | 435/366 |
| 2012/0252110 A1 | 10/2012 | Oura et al. | | |
| 2013/0288344 A1* | 10/2013 | Bargh | ................... | C12M 23/48 |
| | | | | 435/286.1 |
| 2016/0298072 A1* | 10/2016 | Laustsen | ................ | C12M 41/26 |
| 2018/0171278 A1* | 6/2018 | Kiyama | ................. | C12M 27/00 |
| 2019/0211294 A1* | 7/2019 | Karnieli | ................ | C12M 41/48 |
| 2019/0270096 A1* | 9/2019 | Hinz | ...................... | C12M 23/40 |

* cited by examiner

SAMPLE STORAGE APPARATUS

CROSS-REFERENCE TO RELATED APPLICATION

This application claims priority from Japanese Patent Application No. 2018-199369, filed on Oct. 23, 2018, the entire subject matter of which is incorporated herein by reference.

TECHNICAL FIELD

The presently disclosed subject matter relates to a sample storage apparatus.

BACKGROUND

In technical fields in which cells must be cultured, such as regenerative medicine, an apparatus that cultures cells for a long term while maintaining a sterile environment has been developed. In order to check the conditions of cells that are cultured in such an apparatus, a culture solution and the like must be carried out into a non-sterile space while maintaining the sterility of the culture space. In the case where a culture solution in a cell culture vessel is to be subjected to a sampling operation, conventionally, a process must be performed in which a sample in an incubator that is a sterile space is once carried out into a pass box or the like that is disposed adjacently to the incubator, and then taken to the outside, and therefore the sampling operation is troublesome and time-consuming.

As a countermeasure against the problem, a sampling system of the isolator type in which a plurality of cell culture vessels can be accommodated in an incubator that is maintained in a sterile environment has been proposed (for example, JP-A-2012-200239). In the system, in order to maintain a sterile space, a one-way valve that limits a flow of a culture solution to a direction from the inside of the sterile space to the outside is disposed. Thereby the sterility of the interior of an isolator is maintained.

SUMMARY

The conventional sampling system is configured so that a sample is delivered from the sterile space to a non-sterile space by using a pressure which is generated by a tube pump. In the case where an analysis device in which a sample must be stored in a constant amount in a measuring section is used, however, it is difficult to surely store a reference amount of sample in the measuring section in an automatic manner. When the flow path of the analysis device is long, particularly, the sample remains in the middle of the flow path, and it is difficult to store a desired amount of sample. The presently disclosed subject matter provides a novel sample storage apparatus in which, irrespective of the length of a flow path, a desired amount of sample can be recovered.

The inventors have intensively studied the problem, and developed a sample storage apparatus in which a fluid identification sensor is disposed in a flow path connected to a sample storage container, a fluid (such as a sample, the air, or a buffer solution) that is introduced into the sample storage container is identified, the amount of fluid that is introduced into the sample storage container is controlled based on the identification information, and a desired amount of sample can be stored. That is, the presently disclosed subject matter includes the following configurations.

[1] A sample storage apparatus includes:
a lid member;
a sample storage container that is hermetically closable by the lid member;
a first fluid sucking section that is disposed in a side portion of the sample storage container or in the lid member;
a second fluid sucking section that is disposed in the side portion of the sample storage container or in the lid member;
a first fluid discharging section that is disposed in a bottom portion of the sample storage container;
a second fluid discharging section that is disposed in the side portion of the sample storage container or in the lid member;
a first flow path that is connected to the first fluid sucking section, the first flow path being used for connecting with a sampling section;
a second flow path that is connected to the second fluid sucking section, the second flow path communicating with an exterior of the sample storage container;
a third flow path that is connected to the first fluid discharging section, a first fluid discharging unit being disposed in the third flow path;
a fourth flow path that is connected to the second fluid discharging section, a second fluid discharging unit being disposed in the fourth flow path; and
a first fluid identification sensor for identifying a fluid in the first flow path,
wherein the first fluid sucking section or the first flow path has a first opening/closing mechanism, the second fluid sucking section or the second flow path has a second opening/closing mechanism, the first fluid discharging section or the third flow path has a third opening/closing mechanism, the second discharging section or the fourth flow path has a fourth opening/closing mechanism,
wherein the apparatus operates in a manner that, in a case where the first opening/closing mechanism is opened, the second opening/closing mechanism is closed, or, in a case where the second opening/closing mechanism is opened, the first opening/closing mechanism is closed, and,
wherein the apparatus operates in a manner that, in a case where the third opening/closing mechanism is opened, the fourth opening/closing mechanism is closed, or, in a case where the fourth opening/closing mechanism is opened, the third opening/closing mechanism is closed.

According to the presently disclosed subject matter, irrespective of the length of a sampling system, a desired amount of sample can be surely recovered, and also washing of the flow path and the interior of the sample storage container can be surely performed. Therefore, it is possible to construct a sampling system in which a sample that must be sterilely sampled can be automatically recovered.

BRIEF DESCRIPTION OF DRAWINGS

FIGS. 5-2C and 5-2D are diagrams illustrating the usage procedure of a sterile sampling flow path kit that is used in the sample storage apparatus of the other embodiment.

FIG. 6-1 is a diagram illustrating a manner of using the sample storage apparatus of the other embodiment.

FIG. 6-2 is a diagram illustrating a manner of using the sample storage apparatus of the other embodiment.

FIG. 6-3 is a diagram illustrating a manner of using the sample storage apparatus of the other embodiment.

FIG. 6-4 is a diagram illustrating a manner of using the sample storage apparatus of the other embodiment.

FIG. 6-5 is a diagram illustrating a manner of using the sample storage apparatus of the other embodiment.

FIG. 6-6 is a diagram illustrating a manner of using the sample storage apparatus of the other embodiment.

DESCRIPTION OF EMBODIMENTS

Hereinafter, the presently disclosed subject matter will be described by way of embodiments thereof. However, the following embodiments are not intended to limit the presently disclosed subject matter as defined in the appended claims, and all combinations of features described in the embodiments are not always essential to solving means of the presently disclosed subject matter.

1-1. Sample Storage Apparatus (First Mode)

Figure 1:
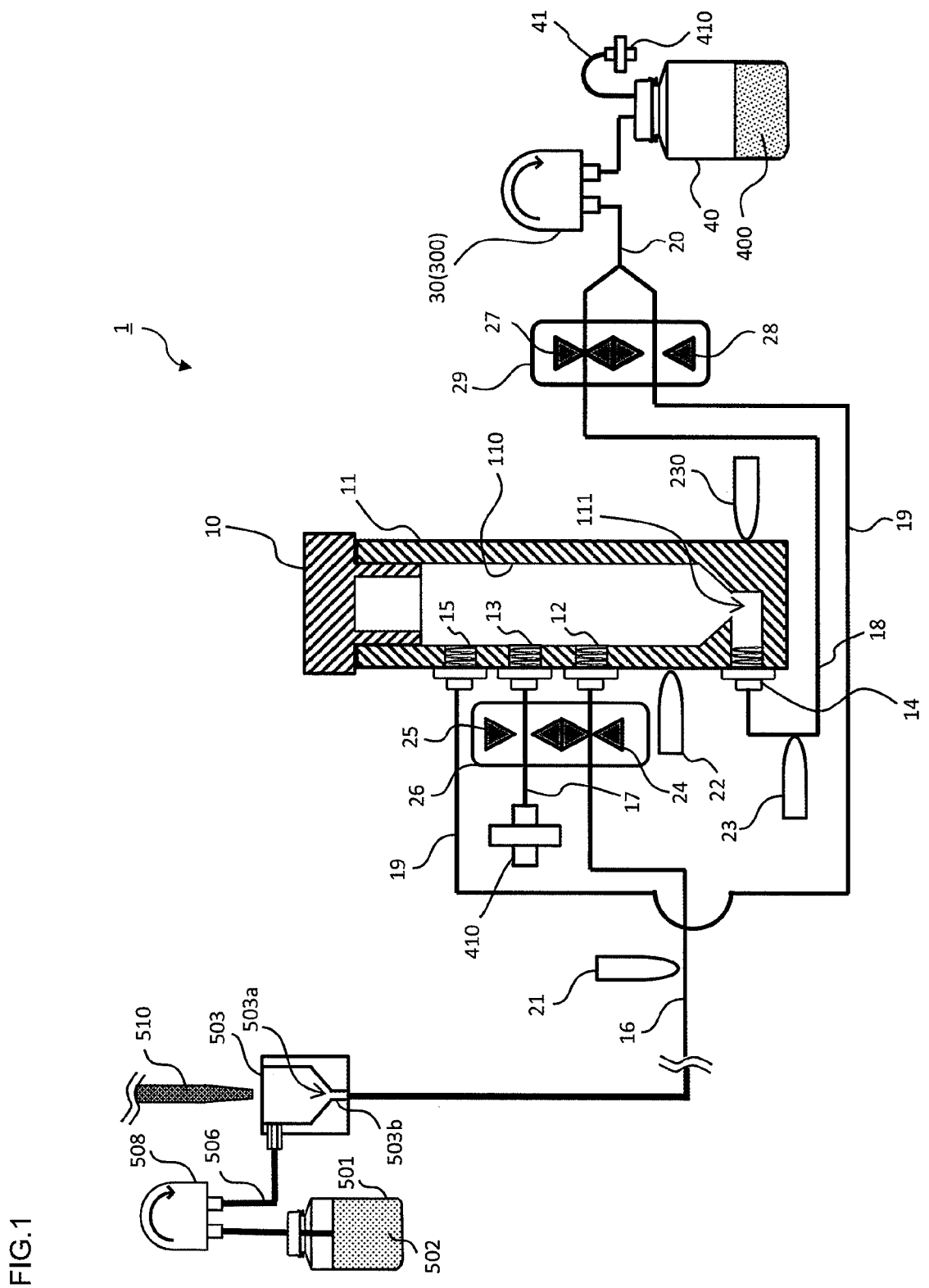
FIG. 1 is a schematic diagram of a sample storage apparatus of an embodiment.

FIG. 1 is a schematic diagram of a sample storage apparatus 1 of an embodiment of the presently disclosed subject matter. In the embodiment, the sample storage apparatus 1 may include:

a lid member 10;

a sample storage container 11 that is hermetically closable by the lid member 10;

a first fluid sucking section 12 that is disposed in a side portion 110 of the sample storage container 11;

a second fluid sucking section 13 that is disposed in the side portion 110 of the sample storage container 11;

a first fluid discharging section 14 that is disposed in a bottom portion 111 of the sample storage container 11;

a second fluid discharging section 15 that is disposed in the side portion 110 of the sample storage container 11;

a first flow path 16 that is connected to the first fluid sucking section 12, the first flow path 16 being used for connecting with a sampling section 503;

a second flow path 17 that is connected to the second fluid sucking section 13, the second flow path 17 communicating with the exterior of the sample storage container 11;

a third flow path 18 that is connected to the first fluid discharging section 14, a first fluid discharging unit 30 being disposed in the third flow path 18;

a fourth flow path 19 that is connected to the second fluid discharging section 15, a second fluid discharging unit 300 being disposed in the fourth flow path 19; and a first fluid identification sensor 21 for identifying a fluid in the first flow path 16, the first flow path 16 may include a first opening/closing mechanism 24, the second flow path 17 may include a second opening/closing mechanism 25, the third flow path 18 may include a third opening/closing mechanism 27, and the fourth flow path 19 may include a fourth opening/closing mechanism 28.

In FIG. 1, the lid member 10 and the sample storage container 11 are illustrated in section. The lid member 10 is attached to or detached from an opening portion of the sample storage container 11, whereby the internal space of the sample storage container 11 can be closed or opened. The lid member 10 is required to hermetically close the sample storage container 11, and may be attached or detached by fitting, screwing, or the like. For example, the lid member 10 is made of a metal (for example, stainless steel), cork, polyethylene, polypropylene, polycarbonate, polystyrene, polyvinyl chloride, nylon, polyurethane, polyurea, polylactate, polyglycolic acid, polyvinyl alcohol, polyvinyl acetate, poly(meta)acrylic acid, a poly(meta)acrylic acid derivative, polyacrylonitrile, poly(meta)acrylamide, a poly(meta)acrylamide derivative, polysulfone, cellulose, a cellulose derivative, glass, or ceramics. A flexible material (for example, a rubber plug (such as natural rubber, synthetic rubber, fluorine rubber, or silicone rubber)) may be used.

The sample storage container 11 can sufficiently accommodate a desired amount of sample. For example, the sample storage container 11 is made of a metal (for example, stainless steel), polyethylene, polypropylene, polycarbonate, polystyrene, polyvinyl chloride, nylon, polyurethane, polyurea, polylactate, polyglycolic acid, polyvinyl alcohol, polyvinyl acetate, poly(meta)acrylic acid, a poly(meta)acrylic acid derivative, polyacrylonitrile, poly(meta)acrylamide, a poly(meta)acrylamide derivative, polysulfone, cellulose, a cellulose derivative, glass, or ceramics. In order to enable a second fluid identification sensor 22 that will be described later, to detect a fluid in the sample storage container 11, however, a transparent or translucent material is preferred.

In the embodiment, the side portion 110 of the sample storage container 11 may include the first fluid sucking section 12, the second fluid sucking section 13, and the second fluid discharging section 15. Each of the first fluid sucking section 12, the second fluid sucking section 13, and the second fluid discharging section 15 may include an opening portion that passes through the exterior to the interior of the sample storage container 11. The first fluid sucking section 12, the second fluid sucking section 13, and the second fluid discharging section 15 are disposed in positions that are higher than the liquid level in the case where a desired amount of sample is accommodated in the sample storage container 11, respectively. The first fluid sucking section 12, the second fluid sucking section 13, and the second fluid discharging section 15 may be disposed in positions that are approximately horizontally arranged, those that are approximately vertically arranged, or those that are randomly dispersed. The positions may be appropriately changed in accordance with the configuration of the whole sampling system. In another embodiment, the first fluid sucking section 12, the second fluid sucking section 13, or the second fluid discharging section 15 may be disposed, for example, in the lid member 10 that is attached to the opening portion of the sample storage container 11.

The bottom portion 111 of the sample storage container 11 may include the first fluid discharging section 14. The bottom portion 111 of the sample storage container 11 is located in a place through which the stored sample or the like easily flows out from the sample storage container 11, and which is coupled to the first fluid discharging section 14. For example, the place may be the lower end of the sample storage container 11, or a place which is inclined from the lower end toward the side portion. The first fluid discharging section 14 may include an opening portion that passes through the exterior to the interior of the sample storage container 11. The sample or buffer solution that is stored in the sample storage container 11 is discharged from the first fluid discharging section 14. Although, in FIG. 1, the first fluid discharging section 14 is disposed in the side portion 110 of the sample storage container 11, the first fluid discharging section may be disposed in the bottom surface of the sample storage container 11. The first fluid discharging section 14 may be appropriately changed in accordance with the configuration of the whole sampling system.

The first flow path 16 is connected to the first fluid sucking section 12. The first flow path 16 is fluidly connected to the sampling section 503 to which the sample is supplied. The first flow path 16 may include the first fluid identification sensor 21 for identifying a fluid passing through the first flow path 16. The first fluid identification sensor 21 can identify the kind of the fluid flowing through the first flow path 16, such as a culture medium containing a sample, a buffer solution, or a gas (for example, the air). A known sensor such as an optical sensor or a proximity sensor can be used as the first fluid identification sensor 21 (this is applicable also to the second fluid identification sensor 22, third fluid identification sensor 23, and fourth fluid identification sensor 230 that will be described later). In the case where an optical sensor is used, for example, a light beam of a predetermined wavelength is orthogonally irradiated on the first flow path 16, and a reflected or transmitted light beam is detected, whereby the kind of the fluid can be identified. In the case where the kind of the fluid flowing through the first flow path 16 is changed (for example, the case where a buffer solution is changed to the air), particularly, a detected signal is largely varied, and therefore it is possible to identify that the kind of the fluid is changed.

One end of the second flow path 17 is connected to the second fluid sucking section 13. A ventilation filter 410 is connected to the other end of the second flow path 17, and the second flow path 17 communicates with the exterior of the sample storage container 11 through the ventilation filter 410. The ventilation filter 410 is requested to prevent the interior of the sample storage container 11 from being contaminated, and not to disturb suction of a fluid (particularly, the air) from the outside of the sample storage container 11, and a commercially available filter may be used as the ventilation filter.

In the embodiment, the third flow path 18 is connected to the first fluid discharging section 14. The first fluid discharging unit 30 for discharging the fluid is disposed in the third flow path 18. When the first fluid discharging unit 30 operates, the fluid (such as a sample, a buffer solution, or the air) stored in the sample storage container 11 can be discharged.

In the embodiment, the fourth flow path 19 is connected to the second fluid discharging section 15. The second fluid discharging unit 300 for discharging the fluid is disposed in the fourth flow path 19. When the second fluid discharging unit 300 operates, the fluid in the sample storage container 11, particularly, gasses (the air and the like) can be discharged.

In the embodiment illustrated in FIG. 1, downstream portions of the third flow path 18 and the fourth flow path 19 are combined and integrated with each other to form a fifth flow path 20. In this case, the first fluid discharging unit 30 and the second fluid discharging unit 300 are identical with each other, and disposed in the fifth flow path 20.

The first fluid discharging unit 30 and/or the second fluid discharging unit 300 may be a tube pump (peristaltic pump), or a piezoelectric pump, and any type of pump can be used as far as it can send a fluid.

In the embodiment, a waste liquid tank 40 is connected to the third flow path 18 (in the mode of FIG. 1, the fifth flow path 20) that is downstream of the first fluid discharging unit 30. A ventilation tube 41 is connected to the waste liquid tank 40, and another ventilation filter 410 is connected to the ventilation tube 41. In the case where the fifth flow path 20 illustrated in FIG. 1 is not provided, the ventilation filter 410 is connected to the fourth flow path 19 that is downstream of the second fluid discharging unit 300.

In the sample storage apparatus 1, the first flow path 16 may include the first opening/closing mechanism 24, the second flow path 17 may include the second opening/closing mechanism 25, the third flow path 18 may include the third opening/closing mechanism 27, and the fourth flow path 19 may include the fourth opening/closing mechanism 28. The first opening/closing mechanism 24, the second opening/closing mechanism 25, the third opening/closing mechanism 27, and the fourth opening/closing mechanism 28 are requested to be mechanisms for opening and closing the respective flow paths, and configured by, for example, opening/closing valves, preferably, or pinch valves. In the case where pinch valves are used, the flow of the fluid in each of the flow paths can be blocked by pinching the flow path. In the embodiment, in the case where the first opening/closing mechanism 24, the second opening/closing mechanism 25, the third opening/closing mechanism 27, and the fourth opening/closing mechanism 28 are configured by pinch valves, the flow paths (the first flow path 16, the second flow path 17, the third flow path 18, and the fourth flow path 19) are preferably configured by tubes that can be sterilized, and that are flexible, respectively, and for example medical tubes (e.g., silicone rubber tubes, polyethylene tubes, polyimide tubes, or fluorine resin tubes) may be employed.

The sample storage apparatus 1 operates in a manner that, in the case where the first opening/closing mechanism 24 is opened, the second opening/closing mechanism 25 is closed, or, in the case where the second opening/closing mechanism 25 is opened, the first opening/closing mechanism 24 is closed. In the embodiment, the first opening/closing mechanism 24 and the second opening/closing mechanism 25 are alternately opened and closed by a first opening/closing switching device 26.

The sample storage apparatus 1 further operates in a manner that, in the case where the third opening/closing mechanism 27 is opened, the fourth opening/closing mechanism 28 is closed, or, in the case where the fourth opening/closing mechanism 28 is opened, the third opening/closing mechanism 27 is closed. In the embodiment, the third opening/closing mechanism 27 and the fourth opening/closing mechanism 28 are alternately opened and closed by a second opening/closing switching device 29.

In the embodiment, first opening/closing switching device 26 and the second opening/closing switching device 29 are configured by, for example, pinch valve switching devices, respectively.

In the embodiment, the sample storage apparatus 1 may further include the second fluid identification sensor 22 in a position which is outside the sample storage container 11, and which is lower than placement of the first fluid sucking section 12, the second fluid sucking section 13, and the second fluid discharging section 15. By using the second fluid identification sensor 22, it is possible to determine whether a sample or a buffer solution is stored in the sample storage container 11, to a necessary-sample amount line 220 (for example, see FIG. 6-1) or not. Moreover, it is possible to prevent the fluid from flowing into the sample storage container 11 more than necessary. The second fluid identification sensor 22 is required to be placed in a position which is lower than placement of the second fluid discharging section 15, and may be placed in a position which is higher than the first fluid sucking section 12 and the second fluid sucking section 13.

In the embodiment, the sample storage apparatus 1 may further include the third fluid identification sensor 23 for identifying a fluid in the third flow path 18. By using the third fluid identification sensor 23, it is possible to check that the fluid (such as a sample or a buffer solution) stored in the sample storage container 11 is surely discharged.

In the embodiment, the sample storage apparatus 1 may further include the fourth fluid identification sensor 230 for identifying a fluid in the periphery of the first fluid discharging section 14. By using the fourth fluid identification sensor 230, it is possible to check the presence or absence of the fluid (such as a sample or a buffer solution) stored in the periphery of the first fluid discharging section 14 of the sample storage container 11.

The sample storage apparatus 1 of the presently disclosed subject matter may be installed in, for example, an incubator, safety cabinet, or isolator that is a known device, or an arbitrary place. Preferably, the sample storage apparatus 1 is used together with a sterile sampling device in which an isolator 6 is used.

Although not illustrated, the sample storage apparatus 1 of the embodiment may further include a controller (for example, a CPU unit) for controlling the first fluid identification sensor 21, the first opening/closing mechanism 24, the second opening/closing mechanism 25, the third opening/closing mechanism 27, the fourth opening/closing mechanism 28, the first fluid discharging unit 30, and the second fluid discharging unit 300. By the controller, the sample storage apparatus 1 can be appropriately controlled, and sampling can be surely performed. The controller may further control the second fluid identification sensor 22, the third fluid identification sensor 23, and the fourth fluid identification sensor 230.

In the embodiment, the lid member 10 has an insertion portion (not illustrated) into which a sample recovering unit 31 is insertable. In the case where the lid member 10 is made of a flexible material (for example, a rubber plug (such as natural rubber, synthetic rubber, fluorine rubber, or silicone rubber)), when the tip end of the sample recovering unit 31 is sharp (for example, see FIG. 6-4), the sample recovering unit 31 can be passed through the lid member 10, and inserted into the sample storage container 11. Because of the restoring force of the flexible material, after the sample recovering unit 31 is taken out, the through hole is closed, and the internal space of the sample storage container 11 can be again maintained to a hermetically sealed state. Preferably, the insertion portion is made of a flexible material, and at least a part of the lid member 10 is made of a flexible material. Moreover, the insertion portion may have a through hole that is smaller in diameter than the sample recovering unit 31.

In the embodiment, an upstream portion of the first flow path 16 is connected to the sampling section 503. The sampling section 503 has an opening portion that fluidly communicates with the first flow path 16 in a direct or indirect manner, and that is used for introducing a sample. The sampling section 503 is fluidly connected to a buffer solution supplying section 501 through a seventh flow path 506. The seventh flow path 506 may include a fourth fluid discharging unit 508, and, when the fourth fluid discharging unit 508 operates, a buffer solution 502 is supplied to the sampling section 503. A tip end portion of a sample supplying unit 510 is inserted into a discharge port 503a of the bottom portion of the sampling section 503. For example, the fourth fluid discharging unit 508 may be configured by a tube pump (peristaltic pump), or a piezoelectric pump, and any type of pump can be used as far as it can send the fluid.

As the buffer solution 502, a solution is useful which has characteristics that suppresses a pH variation to a minimum level in order to prevent the properties of materials contained in the sample SP from being changed. For example, useful are a liquid culture medium (such as DMEM or RPMI-1640) that is used for culture of cells, a phosphate buffer solution, a Tris buffer solution, a HEPES buffer solution, a HEPPS buffer solution, a citrate buffer solution, a boric acid buffer solution, or the like. The kind of the buffer solution 502 may be appropriately selected in accordance with the kind and purpose of the sample SP to be recovered. In place of the buffer solution 502, water or a physiological saline solution may be used.

The sample supplying unit 510 changes the internal air pressure to a negative pressure or a positive pressure, whereby the fluid can be sucked or discharged. For example, a pipette, a tube, or the like can be employed as the fluid supplying unit (for example, see FIGS. 3 and 4). In the case where the sample supplying unit 510 is a pipette, preferably, a tip end portion of the pipette may be a replaceable disposal pipette tip. When a disposal pipette tip is used, the tip can be easily replaced with a new one for every samples, and cross contamination among samples can be prevented from occurring. As a disposal pipette tip, a commercially available one can be used. In accordance with the amount and use of a sample to be handled, for example, useful are pipette tips for capacities of 1 µL, 10 µL, 20 µL, 100 µL, 200 µL, 250 µL, 300 µL, 500 µL, 1,000 µL, 1,200 µL, 2,000 µL, and more. In order to prevent cross contamination among samples from occurring, the sample supplying unit 510 may include a filter.

In another embodiment, although not illustrated, a part of a discharge flow path 503b of the sampling section 503 may include a seal member (for example, an O-ring, a packing, a hollow seal member which is expanded by injecting a gas or a liquid into the inside of the member) that prevents the fluid supplied from the fluid supplying unit 510 from leaking. In this case, a part of a flow path connected to the sampling section 503 has a flow path that is communicable with the atmosphere (for example, includes an opening/closing mechanism), and does not includes, for example, a third fluid discharging unit 36 illustrated in FIG. 3. In the case where the fluid supplying unit 510 is directly inserted into the discharge flow path 503b, the seal member enables the fluid such as a gas or a liquid such as the sample SP or buffer solution 502 that is supplied from the sample supplying unit 510, to be sent into the first flow path 16 while being pressurized.

In another embodiment, the tip end portion of the sample supplying unit 510 may include a flange portion (not illustrated) that covers the discharge port 503a of the sampling section 503. In this case, a seal member (for example, a packing or an O-ring) that prevents the fluid from leaking is disposed in the periphery of the flange portion or the discharge port 503a.

Figure 4:
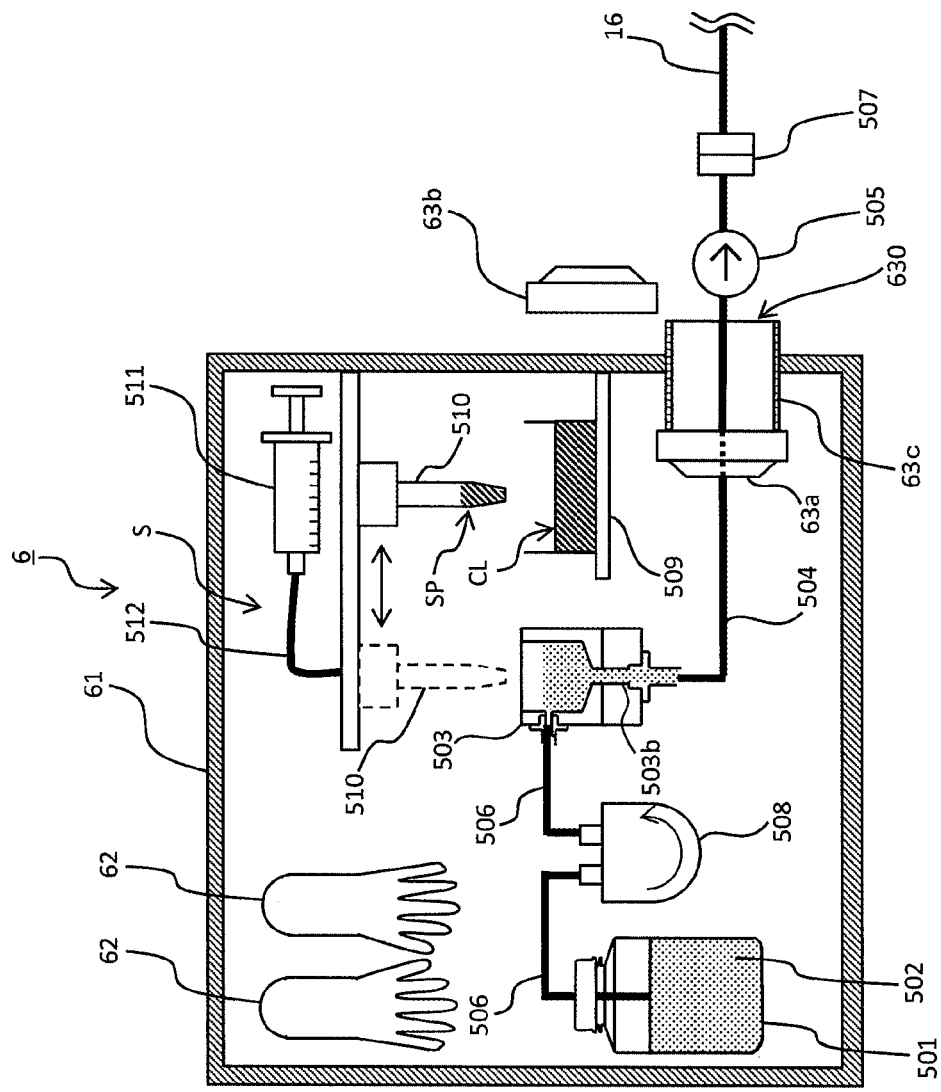
FIG. 4 is a schematic diagram of an isolator that is used in the sample storage apparatus of the other embodiment, and the interior of the isolator.

In the embodiment, the sample supplying unit 510 may include a gas supplying unit 511 (see FIG. 4). The gas supplying unit 511 may include a mechanism which sends a gas G to the sample supplying unit 510. The gas supplying unit 511 is requested to have a mechanism for sending a compressed gas G, and, for example, a syringe or a gas cylinder containing a compressed gas may be used as the gas supplying unit. Preferably, the gas supplying unit may have a function of sucking and discharging a gas. For example, a syringe may be employed. In the case where the gas supplying unit 511 is a syringe, when a piston 511*a* (see FIG. 4) is pulled, the interior of the sample supplying unit 510 is set to have a negative pressure, and the fluid can be sucked into the sample supplying unit 510. When the piston 511*a* is pushed, the compressed gas G can be supplied into the sample supplying unit 510. Preferably, the gas supplying unit 511 is a syringe because both suction and discharge of the fluid can be performed.

Figure 2:
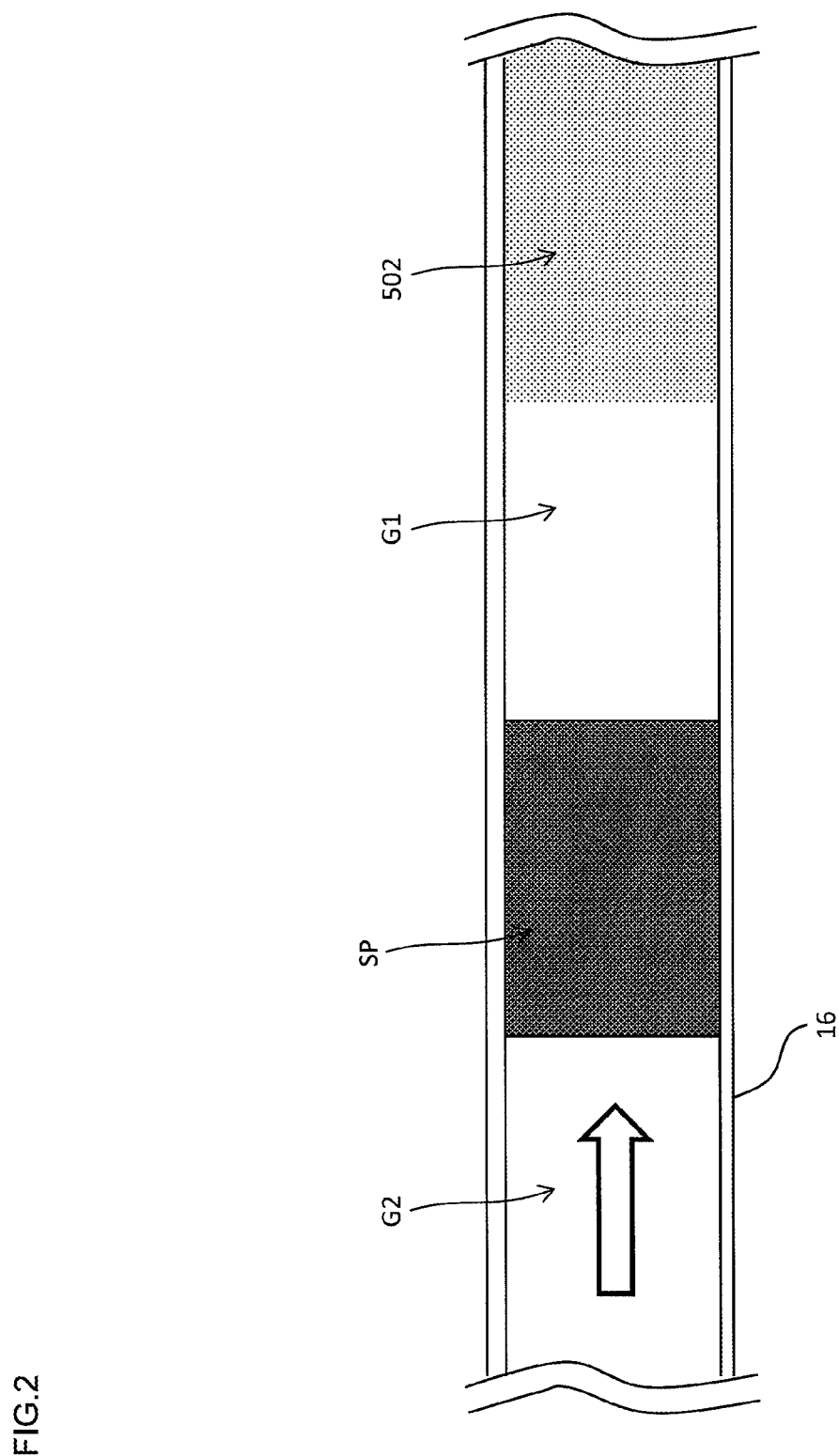
FIG. 2 is a schematic diagram illustrating the interior of a flow path connected to the sample storage apparatus of the embodiment.

FIG. 2 is a view diagrammatically illustrating the manner in which the sample SP, buffer solution 502, and gases (G1 and G2) that are introduced from the sampling section 503 are moved in the first flow path 16. In the first flow path 16 which is washed by the buffer solution 502, the disposition of the region where a first gas G1 exists, behind that where the buffer solution 502 exists can prevent the sample SP and the buffer solution 502 from being mixed with each other. The first gas G1 may be supplied to the region where the first gas G1 exists, by driving an arbitrary fluid discharging unit that is disposed downstream of the first flow path 16, or by the sample supplying unit 510.

In the first flow path 16 where the first gas G1 exists, the sample SP is supplied after the supply of the first gas G1, by the sample supplying unit 510 (step (1)). After the supply of the sample SP in the first flow path 16, then, a second gas G2 is supplied by the sample supplying unit 510 to cause the sample SP to be delivered to the downstream of the first flow path 16 (step (2)). The volume amount of first gas G1 is not limited as far as it has a value at which the buffer solution 502 and the sample SP are not mixed with each other. The volume amount of the gas G2 is requested to have a value at which the sample SP can be moved to a predetermined position of the first flow path 16 or a member that is downstream of the first flow path, and can be appropriately changed. The first gas G1 and the second gas G2 may be any kinds of gasses, and may be the same kind of gas or different kinds of gases as far as the gases can be used for interposing the sample SP therebetween.

1-2. Sample Storage Apparatus (Second Mode)

Figure 3:
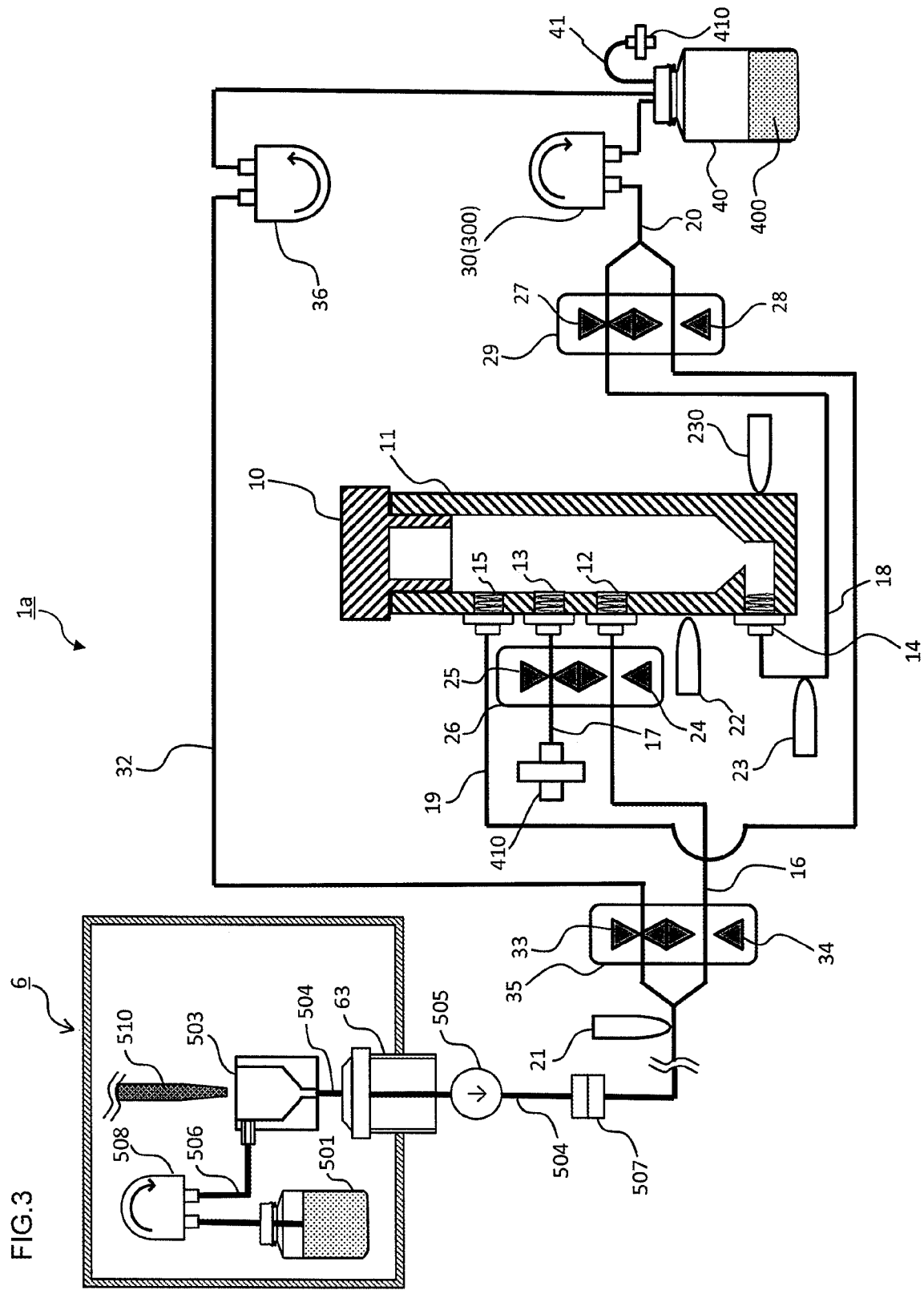
FIG. 3 is a schematic diagram of the sample storage apparatus of another embodiment.

FIG. 3 is a schematic diagram illustrating the sample storage apparatus 1*a* of another embodiment. The configuration of the apparatus is basically identical with the sample storage apparatus 1 of FIG. 1. The components which are indicated by the same reference numerals as those of the sample storage apparatus 1 exert the sane functions that are exerted by those of the sample storage apparatus 1, and therefore their description is omitted.

In addition to the configuration of the sample storage apparatus 1, the sample storage apparatus 1*a* may further include:

a sixth flow path 32 that branches off from the middle of the first flow path 16;

the third fluid discharging unit 36 that is disposed in the sixth flow path 32;

a fifth opening/closing mechanism 33 that is disposed in the sixth flow path 32; and a sixth opening/closing mechanism 34 that is disposed in the first flow path 16.

The fifth opening/closing mechanism 33 and the sixth opening/closing mechanism 34 are requested to be mechanisms for opening and closing the respective flow paths, and configured by, for example, opening/closing valves, preferably, pinch valves, respectively. In the case where pinch valves are used, the flow of the fluid in each of the flow paths can be blocked by pinching the flow path. In the embodiment, in the case where the fifth opening/closing mechanism 33 and the sixth opening/closing mechanism 34 are configured by pinch valves, the flow paths (the first flow path 16 and the sixth flow path 32) are preferably configured by tubes that can be sterilized, and that are flexible, respectively, and for example medical tubes (e.g., silicone rubber tubes, polyethylene tubes, polyimide tubes, or fluorine resin tubes) may be employed.

The sample storage apparatus 1*a* operates in a manner that, in the case where the fifth opening/closing mechanism 33 is opened, the sixth opening/closing mechanism 34 is closed, or, in the case where the sixth opening/closing mechanism 34 is opened, the fifth opening/closing mechanism 33 is closed. In the embodiment, the fifth opening/closing mechanism 33 and the sixth opening/closing mechanism 34 are alternately opened and closed by a third opening/closing switching device 35.

For example, the third fluid discharging unit 36 may be configured by a tube pump (peristaltic pump), or a piezoelectric pump, and any type of pump can be used as far as it can send the fluid.

The sample storage apparatus 1*a* has the sixth flow path 32 that branches off from the middle of the first flow path 16. Even during a period when, for example, the sample stored in the sample storage container 11 is recovered by the sample recovering unit 31, therefore, the buffer solution 502 can be continued to flow into the sampling section 503, and it is possible to maintain the sterility of the internal space of an isolator 6 that will be described later.

Although not illustrated, the sample storage apparatus 1*a* of the embodiment may further include a controller (for example, a CPU unit) for controlling the first fluid identification sensor 21, the first opening/closing mechanism 24, the second opening/closing mechanism 25, the third opening/closing mechanism 27, the fourth opening/closing mechanism 28, the first fluid discharging unit 30, the second fluid discharging unit 300, the third fluid discharging unit 36, the fifth opening/closing mechanism 33, and the sixth opening/closing mechanism 34. By the controller, the sample storage apparatus 1*a* can be appropriately controlled, and sampling can be surely performed.

In the embodiment, the sample storage apparatus 1*a* is configured so that the sampling section 503 is disposed in the isolator 6, and the first flow path 16 is linked with the exterior of the isolator 6 through a liquid delivery port 63 that is disposed in the isolator 6.

The isolator 6 is an apparatus that has a sterile operation area which is completely physically isolated from direct interventions of the environment and an engaged person, that supplies air which is decontaminated, and which is then filtered by a HEPA filter, an ULPA filter, or the like, and that can be continuously used while preventing risk of contamination from the external environment. The isolator 6 in FIG. 3 (or see FIG. 4) is isolated from the external space by a sterile chamber 61, and, although not illustrated, may include a HEPA filter or an ULPA filter. Although not illustrated, the isolator 6 may further include a decontaminating unit that decontaminates the internal space S of the isolator. The term "decontamination" means a process of eliminating living microorganisms by a reproducible method, or that of reducing living microorganisms to a pre-designated level. The decontaminating unit is a unit that is used for realizing "decontamination." For example, a unit using a decontamination agent, that performing a plasma process, that using gamma rays, or that using ultraviolet rays may be employed as the decontaminating unit, but the decontaminating unit is not limited to such units. Preferably, a unit using a decontamination agent may be used. Examples of the decontamination agent are mist or vapor of hydrogen peroxide or peracetic acid, an ozone gas, a chlorine dioxide gas, and an ethylene oxide gas. When such a decontaminating unit is used, the internal space S of the isolator can be decontaminated.

A liquid delivery port body 63c is disposed in the sterile chamber 61 that isolates the inside and outside of the isolator 6 from each other. The liquid delivery port body 63c may have a cylindrical shape, or a hollow rectangular parallelepiped shape. The shape of the liquid delivery port body is not particularly limited. The inside and outside of the sterile chamber 61 communicate with each other through the liquid delivery port body 63c. A liquid delivery port inner lid 63a and a liquid delivery port outer lid 63b can be fitted to liquid delivery port openings 631, 630 of the liquid delivery port body 63c, respectively to hermetically close the liquid delivery port openings 631, 630. The liquid delivery port 63 may include at least the liquid delivery port inner lid 63a, the liquid delivery port outer lid 63b, and the liquid delivery port body 63c. An eighth flow path 504 is passed through the liquid delivery port inner lid 63a. The portion of the liquid delivery port inner lid 63a through which the eighth flow path 504 is passed is sealed by a sealing member or the like so that the fluid does not leak.

The eighth flow path 504 communicates with the discharge flow path 503b of the sampling section 503. The sample or buffer solution 502 that is supplied to the sampling section 503 passes through the eighth flow path 504 that communicates with the discharge flow path 503b of the sampling section 503, is then discharged to the outside of the isolator 6, and thereafter is sent to the first flow path 16 that is fluidly connected to the eighth flow path 504.

In the embodiment, the eighth flow path 504 may include at least one one-way valve 505 that limits movement of the fluid in the eighth flow path 504 to a direction from the sampling section 503 toward the liquid delivery port 63. This can prevent the fluid from reversely flowing toward the interior of the isolator 6.

Preferably, the inner walls of the all flow paths (the first to eighth flow paths) that are used in the presently disclosed subject matter have a low liquid wettability, i.e., have a hydrophobic property. Even in the case where the amount of sample SP is small, this can prevent the sample SP from adhering to the inner walls of the flow paths, and therefore the sample SP can be efficiently delivered to the outside of the isolator 6. As the flow paths that are used in the presently disclosed subject matter, tubes that can be sterilized, and that are flexible may be used, and for example medical tubes (e.g., silicone rubber tubes, polyethylene tubes, polyimide tubes, or fluorine resin tubes) may be employed.

In the embodiment, the eighth flow path 504 may include a sterile connection coupling 507 in the middle of the flow path. In the sterile connection coupling 507, a sterile connection coupling (male type) 507a and a sterile connection coupling (female type) 507b are combined with each other, membrane strips 5070 that hermetically close openings of the sterile connection coupling (male type) 507a and the sterile connection coupling (female type) 507b, respectively are pulled and peeled off, and the sterile connection coupling (male type) 507a and the sterile connection coupling (female type) 507b are locked with each other, whereby the two couplings can be sterilely coupled to each other. As the sterile connection coupling 507, a commercially available one can be used. For example, the coupling is available from Pall Corporation (USA), Sartorius AG (Germany), Colder Products Company (USA), or the like. The sterile connection coupling (male type) 507a and the sterile connection coupling (female type) 507b may be exchangedly used.

When the sterile connection coupling (male type) 507a (or the sterile connection coupling (female type) 507b) is disposed in the middle of the eighth flow path 504 and downstream of the liquid delivery port inner lid 63a, the flow path which sterilely connects the inside and outside of the isolator to each other can be minimized. The sterile connection coupling 507 enables the flow path downstream of the sterile connection coupling 507 to be freely designed.

The presently disclosed subject matter further includes the following configurations.

[2] The sample storage apparatus according to [1], further includes a second fluid identification sensor in a position that is outside the sample storage container and that is lower than placement of the second fluid discharging section.

[3] The sample storage apparatus according to [1], further includes a third fluid identification sensor for identifying a fluid in the third flow path.

[4] The sample storage apparatus according to [1], further includes a fourth fluid identification sensor for identifying a fluid in a periphery of the first fluid discharging section.

[5] The sample storage apparatus according to [1], wherein the first fluid discharging unit and the second fluid discharging unit are tube pumps or piezoelectric pumps.

[6] The sample storage apparatus according to [1], further includes a fifth flow path in which downstream portions of the third and fourth flow paths are combined and integrated with each other, wherein the first fluid discharging unit is identical with the second fluid discharging unit, and the first fluid discharging unit is disposed in the fifth flow path.

[7] The sample storage apparatus according to [1], further includes:

a sixth flow path that branches off from a middle of the first flow path;

a third fluid discharging unit that is disposed in the sixth flow path;

a fifth opening/closing mechanism that is disposed in the sixth flow path; and a sixth opening/closing mechanism that is disposed in the first flow path, wherein the apparatus operates in a manner that, in a case where the fifth opening/closing mechanism is opened, the sixth opening/closing mechanism is closed, or, in a case where the sixth opening/closing mechanism is opened, the fifth opening/closing mechanism is closed.

[8] The sample storage apparatus according to [1], further includes a controller for controlling the first fluid identification sensor, the first opening/closing mechanism, the second opening/closing mechanism, the third opening/closing mechanism, the fourth opening/closing mechanism, the first fluid discharging unit, and the second fluid discharging unit.

[9] The sample storage apparatus according to [7], further includes a controller for controlling the first fluid identification sensor, the first opening/closing mechanism, the second opening/closing mechanism, the third opening/closing mechanism, the fourth opening/closing mechanism, the first fluid discharging unit, the second fluid discharging unit, the third fluid discharging unit, the fifth opening/closing mechanism, and the sixth opening/closing mechanism.

[10] The sample storage apparatus according to [1], wherein the lid member has an insertion portion into which a sample recovering unit is insertable.

[11] The sample storage apparatus according to [1], wherein an upstream portion of the first flow path is connected to the sampling section.

[12] The sample storage apparatus according to [11], wherein the sampling section is disposed in an isolator, and the first flow path is linked with an exterior of the isolator through a liquid delivery port that is disposed in the isolator.

[13] The sample storage apparatus according to [11], further includes a sample supplying unit for supplying a sample to the sampling section.

[14] The sample storage apparatus according to [11], further includes:

a seventh flow path that communicates with the sampling section;

a buffer solution supplying section for supplying a buffer solution to the seventh flow path; and a fourth fluid discharging unit that is disposed in the seventh flow path.

[15] The sample storage apparatus according to [1], wherein the first flow path includes at least one one-way valve that limits movement of a fluid passing through the first flow path to a direction from the sampling section toward the sample storage container.

[16] The sample storage apparatus according to [1], wherein the apparatus further includes a sterile connection coupling in the first flow path.

Figures 1A, 5:
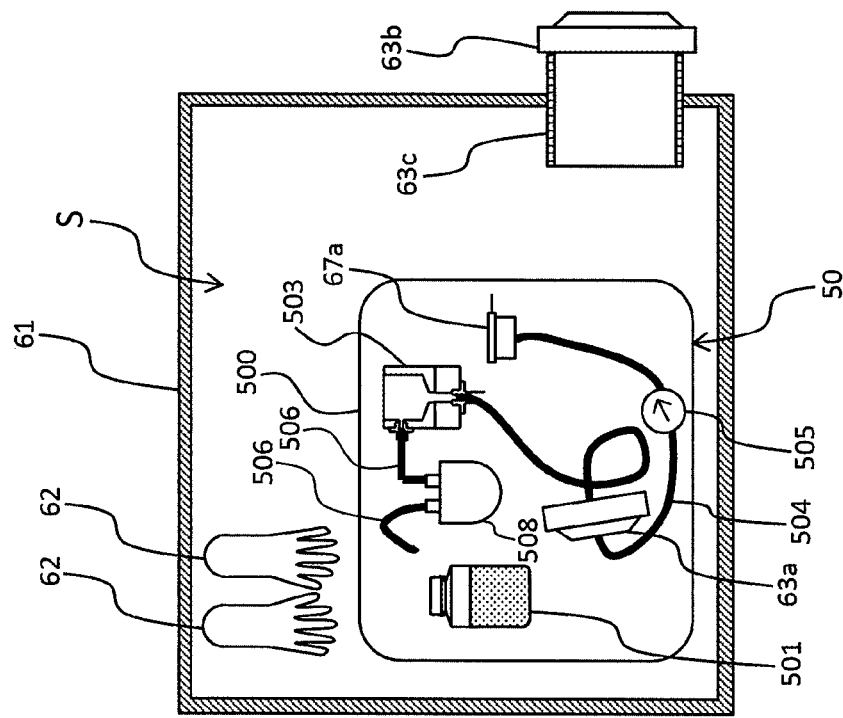
FIGS. 5-1A and 5-1B are diagrams illustrating the usage procedure of a sterile sampling flow path kit that is used in the sample storage apparatus of the other embodiment.
Figures 1B, 5:
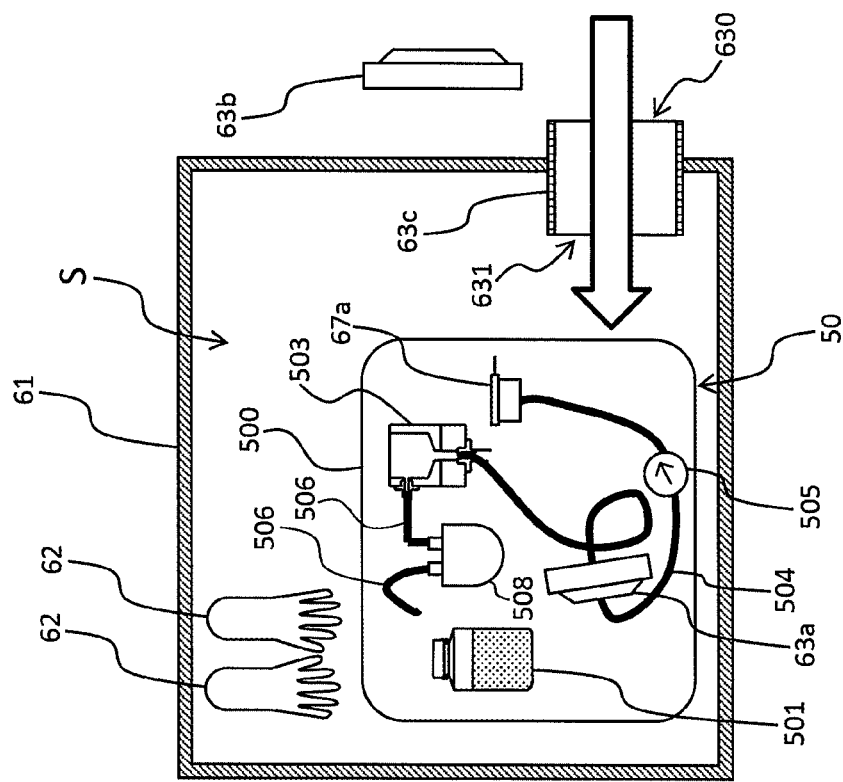
Figures 2D, 5:
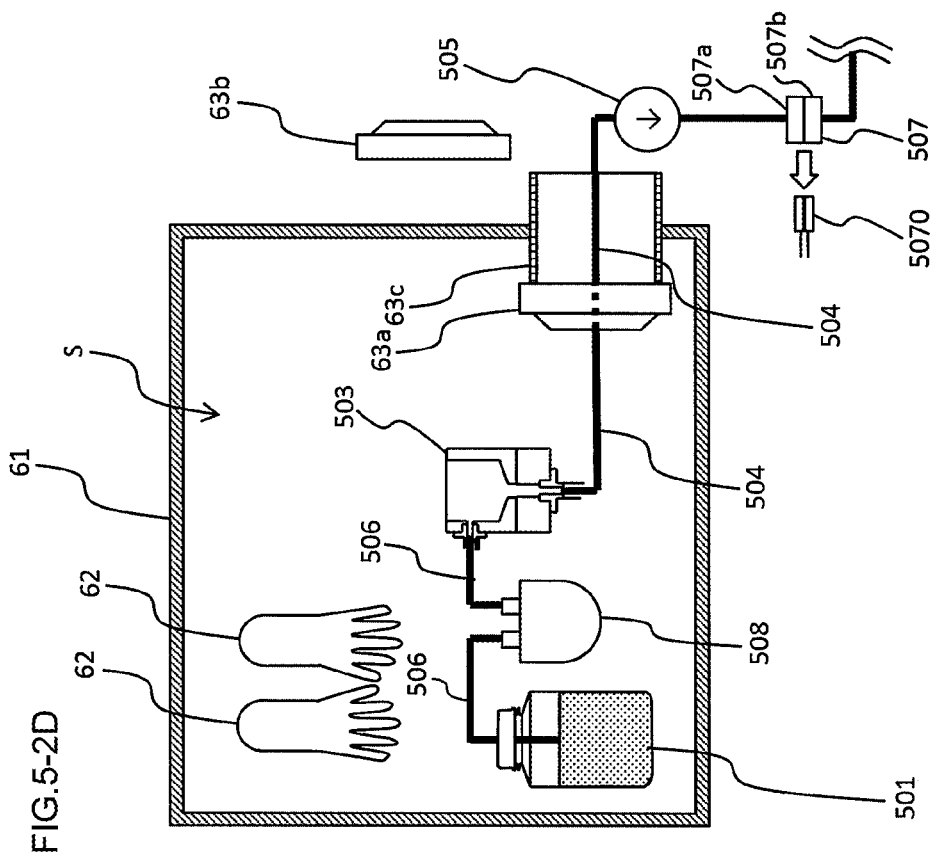

2. Usage Procedure of Sterile Sampling Flow Path Kit Used in Sample Storage Apparatus The procedure for preparing a state where, in the embodiment, the sample storage apparatus 1a can be used will be described (FIGS. 5-1A to 5-2D).

The sample storage apparatus 1a of the presently disclosed subject matter can use a sterile sampling flow path kit 50. In the embodiment, the sterile sampling flow path kit 50 may include:

the sampling section 503;

the eighth flow path 504 that communicates with the sampling section 503; and the at least one one-way valve 505 that is disposed in the eighth flow path 504, and that limits movement of the fluid in the eighth flow path 504 to the direction from the sampling section 503 toward the liquid delivery port 63.

In another embodiment, as illustrated in FIG. 5-1A, the sterile sampling flow path kit 50 may further include: the seventh flow path 506 that communicates with the sampling section 503; the buffer solution supplying section 501 that supplies the fluid to the seventh flow path 506; and the fourth fluid discharging unit 508 that is disposed in the seventh flow path 506. In the other embodiment, the sterile sampling flow path kit 50 may further include a sterile connection coupling in the downstream end of the eighth flow path 504. The above-described members included in the sterile sampling flow path kit 50 may be enclosed in individual sterile bags 500, respectively, or collectively enclosed in the same sterile bag 500 as illustrated in FIG. 5-1A. The members of the sterile sampling flow path kit 50 that are enclosed in the sterile bag 500 are previously sterilized by gamma rays, electron beams, or the like.

The above-described sterile sampling flow path kit 50 is carried in into the isolator 6 through the openings of the liquid delivery port body 63c of the isolator 6, or a decontamination pass box (not illustrated) that is additionally disposed in the isolator 6 (FIG. 5-1A). Thereafter, the liquid delivery port opening 63o that is on the outer side is hermetically closed with the liquid delivery port outer lid 63b, and the interior of the isolator 6 and the sterile sampling flow path kit 50 are decontaminated (FIG. 5-1B). The liquid delivery port inner lid 63a may be provided in the state where the lid is enclosed in the sterile bag 500 as illustrated in FIGS. 5-1A and 1B, or provided into the isolator 6 separately from the sterile bag 500.

Figures 2C, 5:
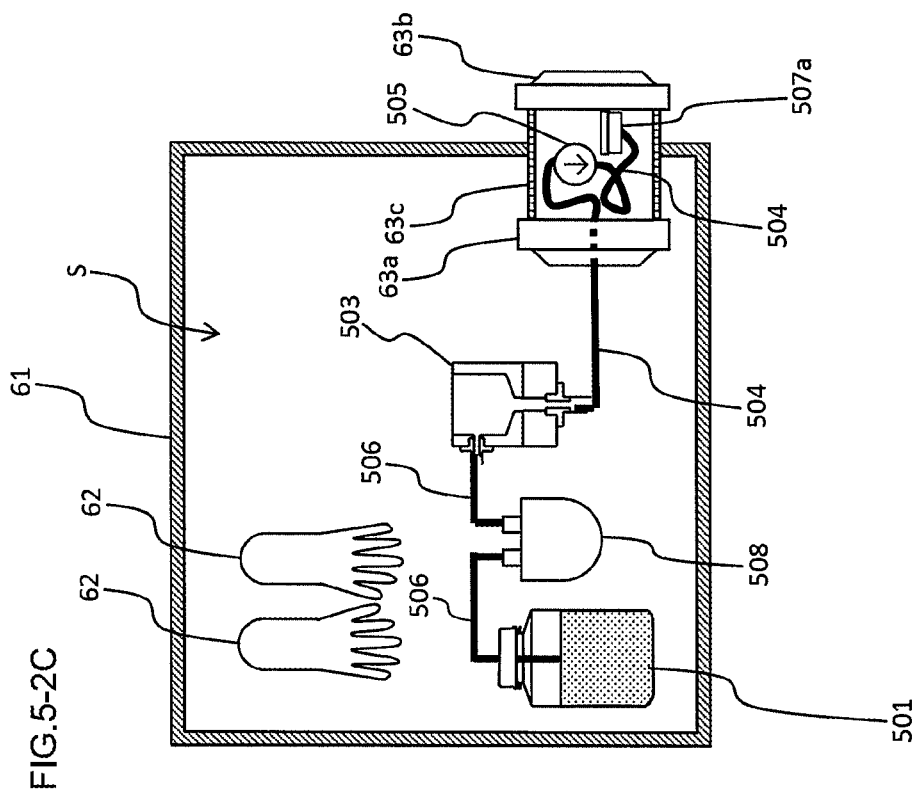

After the decontamination is completed, the sterile bag 500 is opened by using gloves 62 into which the arms of the operator can be inserted from the outside of the isolator 6, and the members are assembled together. The eighth flow path 504, the one-way valve 505, and the sterile connection coupling (male type) 507a are placed in the liquid delivery port body 63c, and the liquid delivery port body is hermetically closed with the liquid delivery port inner lid 63a through which the eighth flow path 504 is passed (FIG. 5-2C). From the outside of the isolator 6, the liquid delivery port outer lid 63b is detached, and the eighth flow path 504, the one-way valve 505, and the sterile connection coupling (male type) 507a are taken out from the liquid delivery port body 63c. Thereafter, the coupling is sterilely coupled to the first flow path 16 which has the sterile connection coupling (female type) 507b at one end, by using the sterile connection coupling 507. As a result, the sterile sampling apparatus 1a of the presently disclosed subject matter and using the sterile sampling flow path kit can be used.

3. Method of Storing Sample by Using Sample Storage Apparatus

Figures 1, 6:
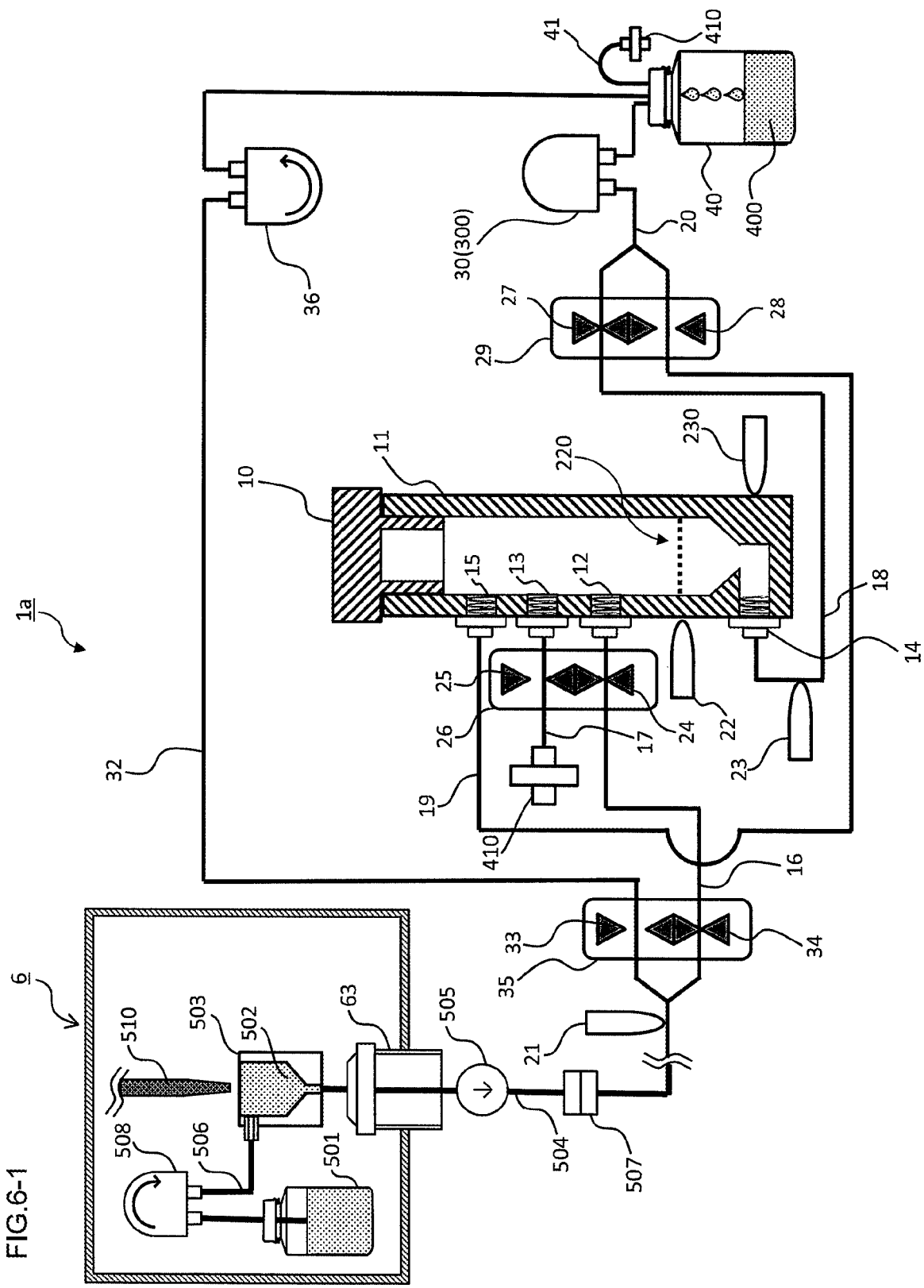
Figures 2, 6:
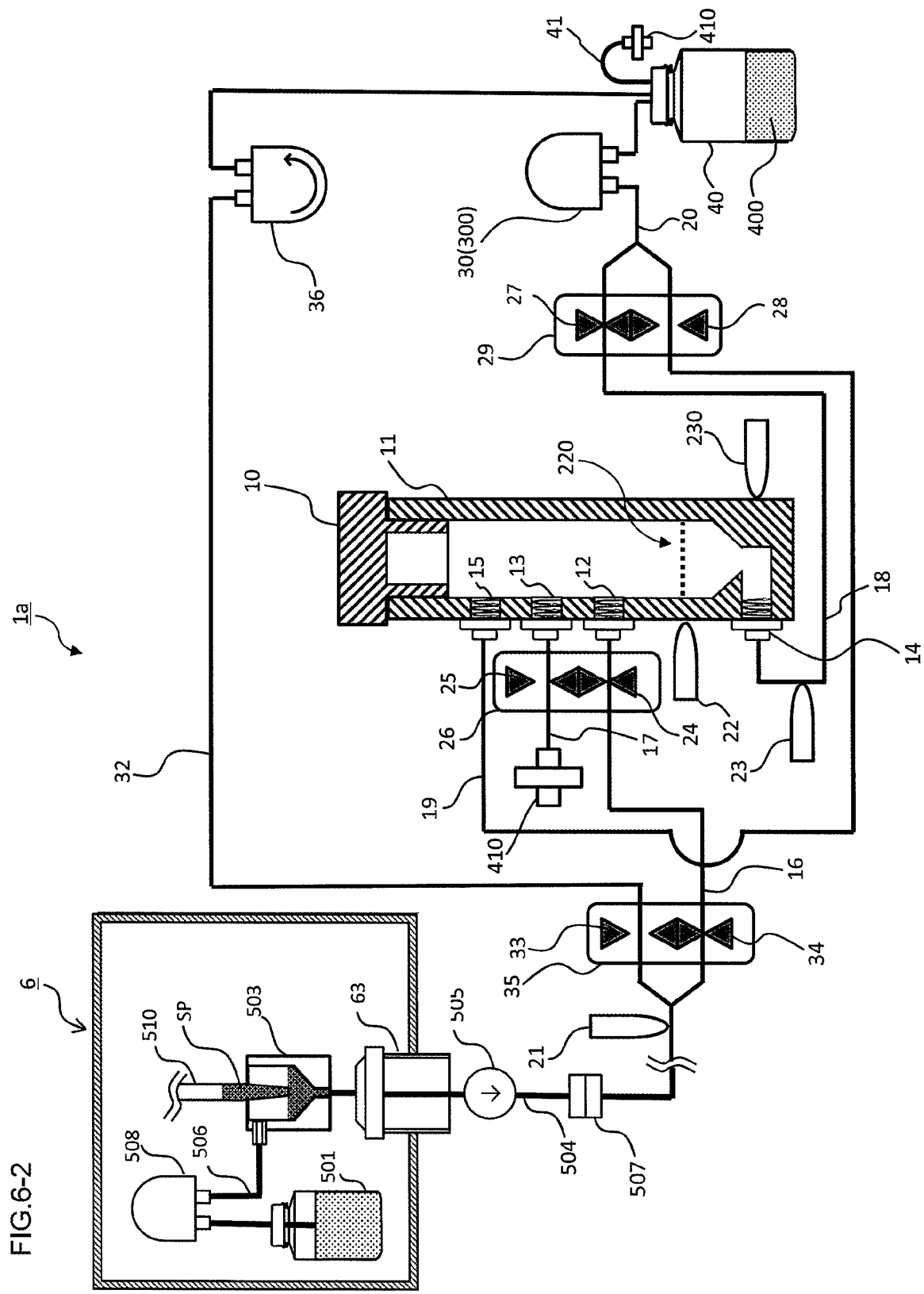
Figures 3, 6:
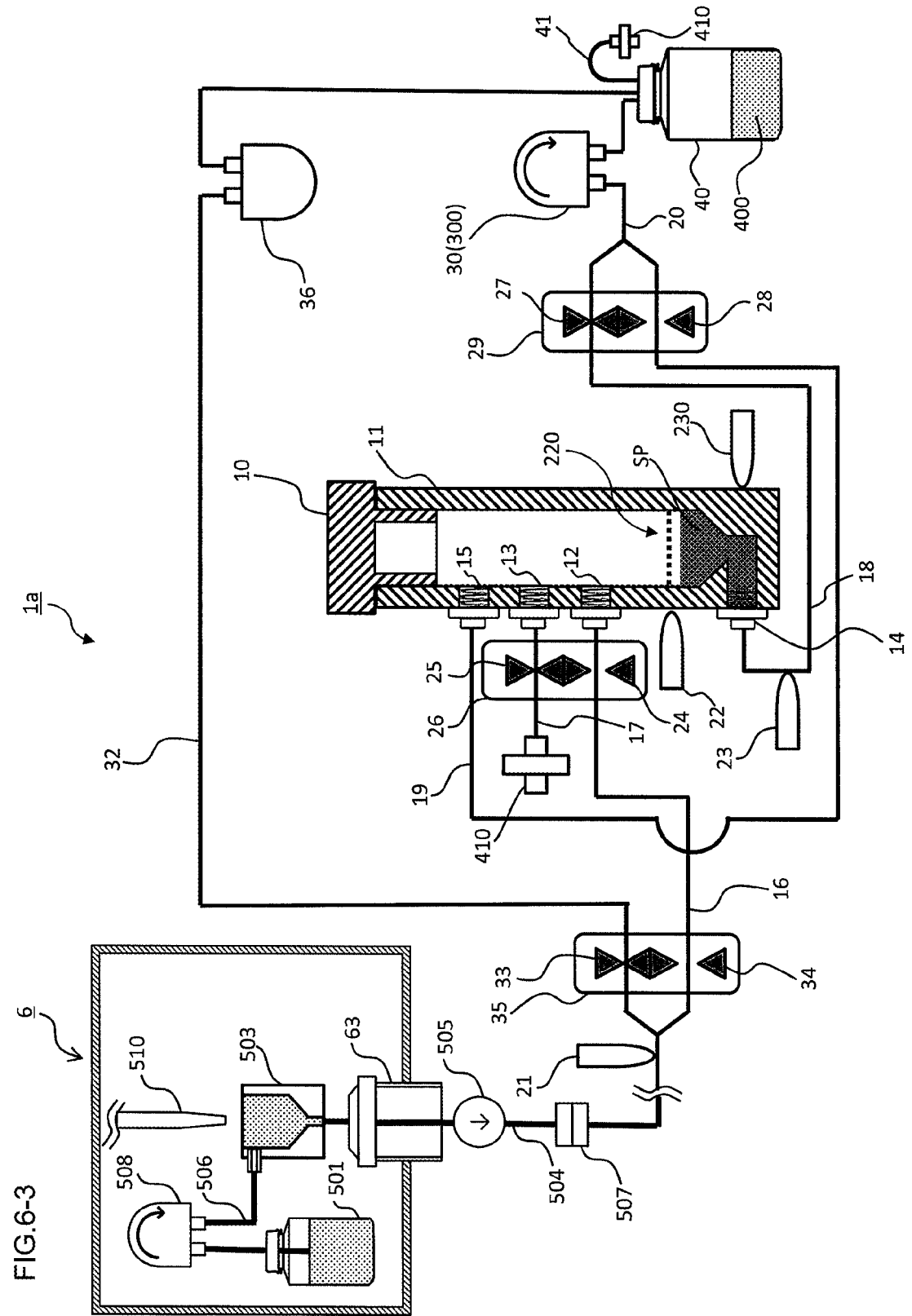
Figures 4, 6:
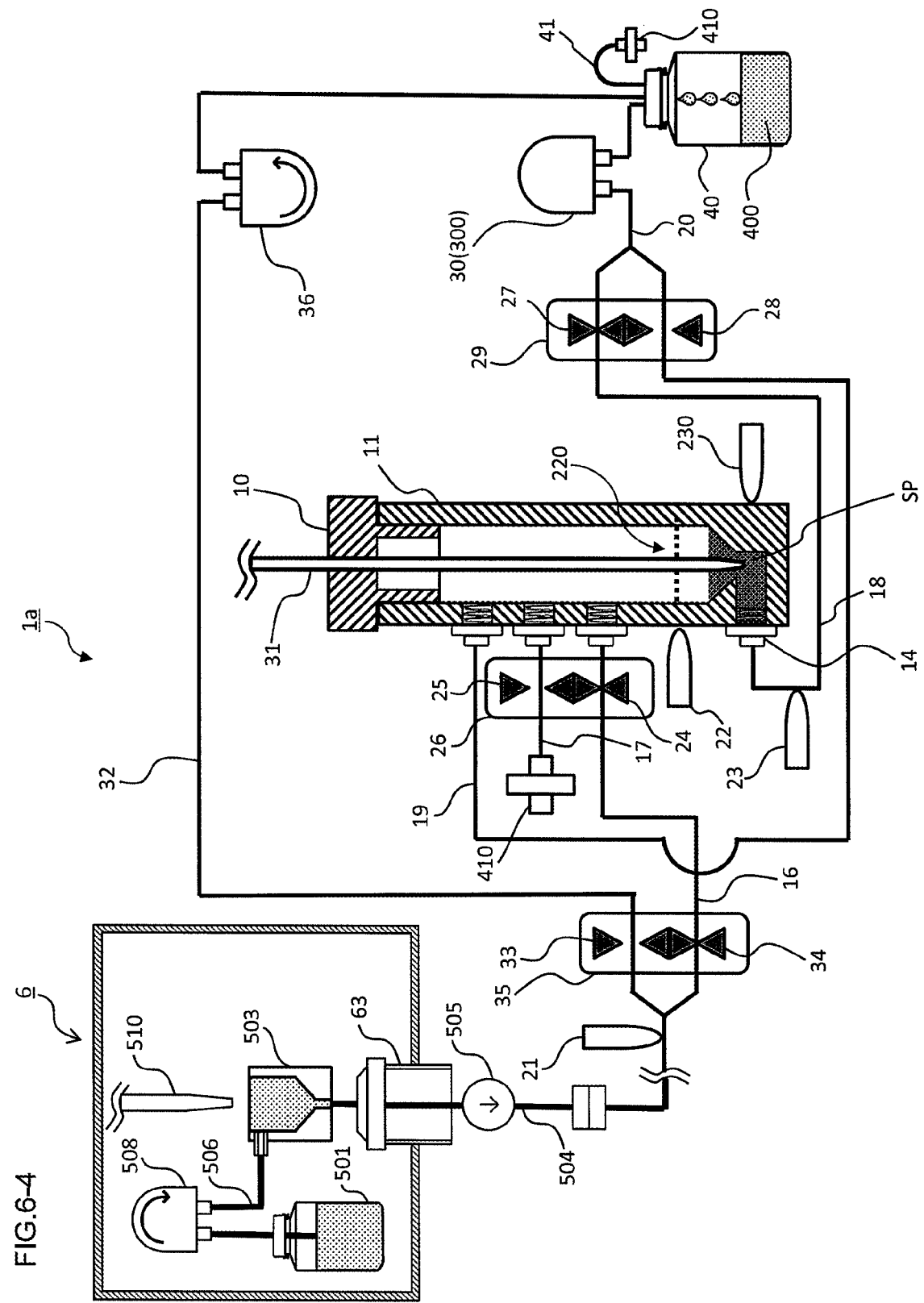
Figures 5, 6:
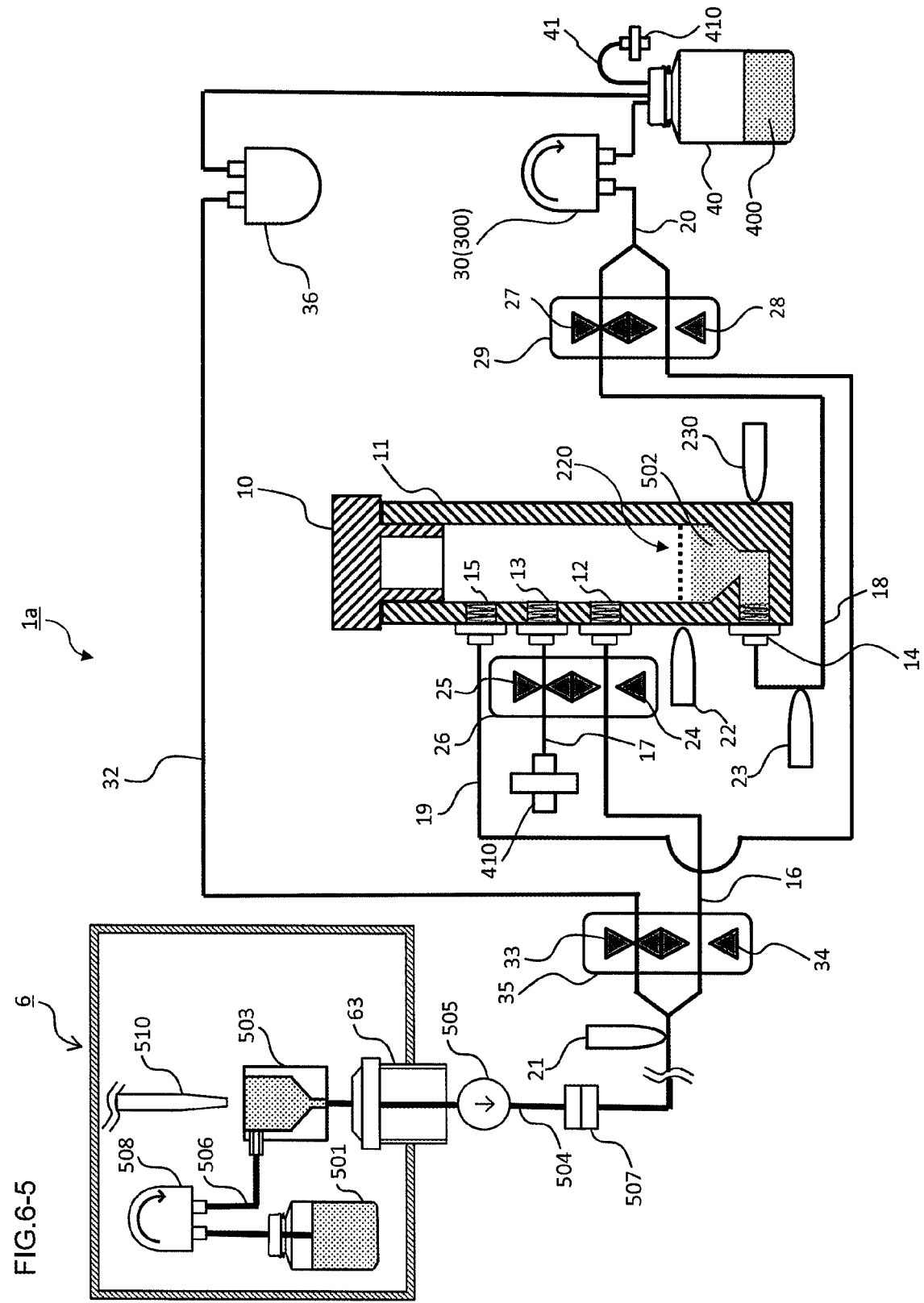
Figure 6:
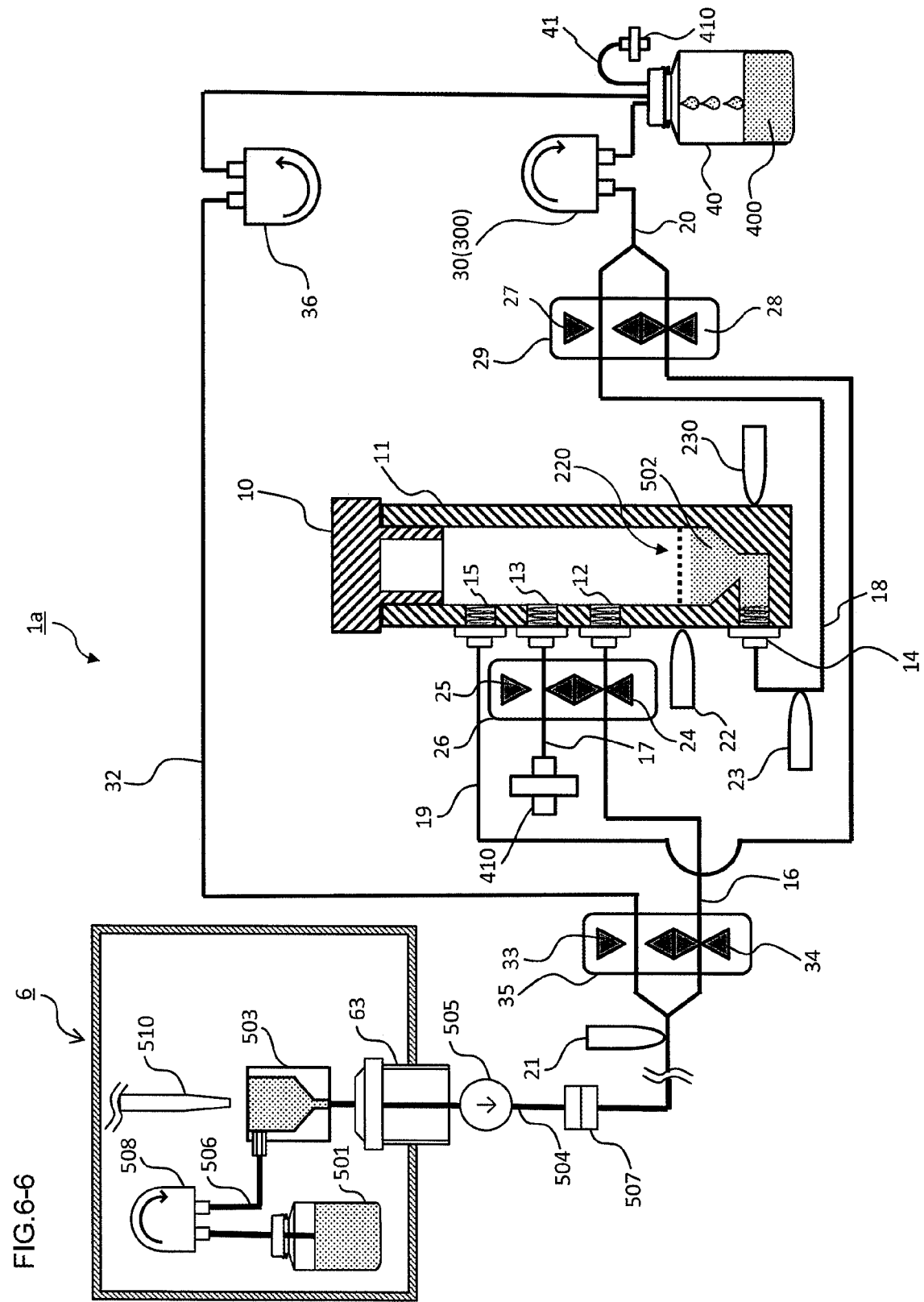

FIGS. 6-1 to 6-6 are diagrams illustrating a usage manner of the sample storage apparatus 1a of the embodiment.

A method of storing a sample by using the sample storage apparatus 1a connected to the sampling section 503 that is disposed in the isolator 6 in accordance with 2, above will be described with reference to the figures and the following table.

TABLE 1

| | | Operating member (abbreviation) Reference numeral | | | | | | | | |
|---|---|---|---|---|---|---|---|---|---|---|
| | Step | Pump for buffer solution 508 | Pump (1) 36 | Pump (2) 30 | Valve (1) 35 | Valve (2) 26 | Valve (3) 29 | Sensor (1) 21 | Sensor (2) 22 | Sensor (3) 23 | Reference figure |
| #1 | Buffer solution | ON | ON | OFF | Upper | Upper | Lower | L | A | A | FIG. 6-1 |
| #2 | Air layer | OFF | ON | OFF | Upper | Upper | Lower | L | A | A | |
| #3 | Sample injection | OFF | ON | OFF | Upper | Upper | Lower | L | A | A | FIG. 6-2 |
| #4 | Air detection | OFF | ON | OFF | Upper | Upper | Lower | A | A | A | |
| #5 | Sample detection | OFF | ON | OFF | Upper | Upper | Lower | L | A | A | |
| #6 | Sample suction | OFF | OFF | ON | Lower | Lower | Upper | L | A | A | |
| #7 | Sample storage | ON | OFF | ON | Lower | Lower | Lower | A | L | A | FIG. 6-3 |
| #8 | Sample measurement | ON | ON | OFF | Upper | Upper | Lower | L | L | A | FIG. 6-4 |
| #9 | Sample discharge | ON | ON | ON | Upper | Upper | Upper | L | A | L | |
| #10 | Comp. of sample discharge | ON | ON | ON | Upper | Upper | Upper | L | A | A | |

TABLE 1-continued

| | | Operating member (abbreviation) Reference numeral | | | | | | | | |
|---|---|---|---|---|---|---|---|---|---|---|
| | Step | Pump for buffer solution 508 | Pump (1) 36 | Pump (2) 30 | Valve (1) 35 | Valve (2) 26 | Valve (3) 29 | Sensor (1) 21 | Sensor (2) 22 | Sensor (3) 23 | Reference figure |
| #11 | Buffer solution storage (wash) | ON | OFF | ON | Lower | Lower | Lower | L | L | A | FIG. 6-5 |
| #12 | Buffer sol. discharge (wash)) (wash) | ON | ON | ON | Upper | Upper | Upper | L | A | A | FIG. 6-6 |
| #13 | Buffer solution | ON | ON | OFF | Upper | Upper | Lower | L | A | A | FIG. 6-1 |

In Table 1, "Operating member" means the members of the sample storage apparatus 1a that are caused to operate in respective steps. The members are abbreviated in Table 1. The reference numerals of the members correspond to the numerals that are listed below "Operating member," and coincide with the reference numerals which are described above.

In Table 1, "Pump for buffer solution," "Pump (1)," and "Pump (2)" indicate "fourth fluid discharging unit 508," "third fluid discharging unit 36," and "first fluid discharging unit 30," respectively. "ON" indicates that the corresponding pump is operating, and "OFF" indicates that the corresponding pump is not operating.

In Table 1, "Valve (1)," "Valve (2)," and "Valve (3)" indicate "third opening/closing switching device 35," "first opening/closing switching device 26," and "second opening/closing switching device 29," respectively. The terms "Upper" and "Lower" in Table 1 indicate the positions of the opening/closing mechanisms in each of which the opened opening/closing mechanism exists in the piping diagrams of FIGS. 6-1 to 6-6. When "Valve (1)" is "Upper," for example, it indicates the state where the fifth opening/closing mechanism 33 is "opened," and the sixth opening/closing mechanism 34 is "closed."

In Table 1, "Sensor (1)," "Sensor (2)," and "Sensor (3)" indicate "first fluid identification sensor 21," "second fluid identification sensor 22," and "third fluid identification sensor 23," respectively. "Sensor (1)" determines whether the fluid is a buffer solution, the air, or a sample. "Sensor (2)" determines whether a desired liquid is stored to the necessary-sample amount line or not. "Sensor (3)" determines whether the liquid is discharged from the sample storage container 11 or not. In Table 1, "L" indicates that "liquid" is detected, and "A" indicates that "air" is detected.

The steps will be described with dividing them into Steps 1 to 13.

Step 1. Buffer Solution (Perfusion):

In this step, the buffer solution 502 is continuously supplied to the sampling section 503, and then discharged into the waste liquid tank 40 through the sixth flow path 32 (see FIG. 6-1). In the case where, during cultivation of cells in the isolator 6, the step is executed, the interior of the isolator 6 is prevented from being contaminated.

Step 2. Air Layer (Introduction):

The pump for the buffer solution is stopped, and, by the action of the pump (1), the air in the isolator 6 is introduced into the eighth flow path 504 through the sampling section 503.

Step 3. Sample Injection:

After, in Step 2, a desired amount of air is introduced into the eighth flow path 504, Step 3 is executed. The sample contained in the sample supplying unit 510 is ejected to the sampling section 503, and the sample is injected (see FIG. 6-2).

Step 4. Air Layer Detection:

The air layer that is introduced in Step 2 is detected by Sensor (1).

Step 5. Sample Detection:

The sample that is introduced in Step 3 is detected by Sensor (1).

Step 6. Sample Suction:

After Step 5, Valve (1), Valve (2), and Valve (3) are switched, and the sample is introduced into the sample storage container 11 through the first flow path 16.

Step 7. Sample Storage:

The air layer is detected by Sensor (1), thereby detecting the end of the sample. Thereafter, the pump for the buffer solution is operated, and the buffer solution 502 is introduced into the sampling section 503. This step is continued until Sensor (2) detects that the sample is stored to the necessary-sample amount line (see FIG. 6-3).

Step 8. Sample Measurement:

The sample recovering unit 31 is inserted through the insertion portion of the lid member 10, and the sample is recovered (as required, desired characteristics of the sample are measured). At this time, the buffer solution 502 is continuously supplied to the sampling section 503, and then discharged into the waste liquid tank 40 through the sixth flow path 32, thereby maintaining the sterility of the interior of the isolator 6 (FIG. 6-4).

Step 9. Sample Discharge:

After Step 8 is ended, the remaining sample is discharged from the first fluid discharging section 14 of the sample storage container 11.

Step 10. Completion of Sample Discharge:

When Sensor (3) detects the air layer, the sample discharge is completed.

Step 11. Buffer Solution Storage (Wash):

The buffer solution 502 is stored in the sample storage container 11. The storage is continued until Sensor (2) detects that the buffer solution 502 is stored to the necessary-sample amount line (see FIG. 6-5).

Step 12. Buffer Solution Discharge (Wash):

The buffer solution 502 is discharged from the first fluid discharging section 14 of the sample storage container 11. When Sensor (3) detects the air layer, the step is ended (see FIG. 6-6).

Step 13. Buffer Solution (Perfusion):

This step is basically same as or similar to Step 1 above.

When Steps 1 to 13 are executed, the desired sample can be recovered at a desired timing while securing the sterility of the interior of the isolator 6. In Steps 1 to 13 above, an arbitrary step(s) may be repeated. When Steps 11 and 12 are repeated a desired number of times, the sample that remains in the sample storage container 11 can be sufficiently washed away.

Steps 1 to 13 above may be controlled by the above-described controller, and it is possible to realize an automatic sampling apparatus that can automatically perform sampling.

Although the presently disclosed subject matter has been described by way of the embodiments, the technical scope of the presently disclosed subject matter is not restricted to the scope of the description of the embodiments. It is obvious to those skilled in the art that various changes or improvements can be made on the embodiments.

What is claimed is:

1. A sample storage apparatus comprising:
    a lid member;
    a sample storage container that is hermetically closable by the lid member;
    a first fluid sucking section that is configured to suck fluid into the sample storage container and is disposed in a side wall of the sample storage container;
    a second fluid sucking section that is configured to suck fluid into the sample storage container and is disposed in the side wall of the sample storage container;
    a first fluid discharging section that is disposed in a bottom portion of the sample storage container;
    a second fluid discharging section that is disposed in the side wall of the sample storage container;
    a first flow path that is connected to the first fluid sucking section, the first flow path being used for connecting with a sampling section;
    a second flow path that is connected to the second fluid sucking section, the second flow path communicating with an exterior of the sample storage container;
    a third flow path that is connected to the first fluid discharging section;
    a fourth flow path that is connected to the second fluid discharging section;
    at least one fluid discharging unit that receives fluid from the third flow path and the fourth flow path; and
    a first fluid identification sensor for identifying a fluid in the first flow path,
    wherein the first flow path has a first opening/closing mechanism, the second flow path has a second opening/closing mechanism, the third flow path has a third opening/closing mechanism, the fourth flow path has a fourth opening/closing mechanism,
    wherein the apparatus operates in a manner that, in a case where the first opening/closing mechanism is opened, the second opening/closing mechanism is closed, or, in a case where the second opening/closing mechanism is opened, the first opening/closing mechanism is closed, and,
    wherein the apparatus operates in a manner that, in a case where the third opening/closing mechanism is opened, the fourth opening/closing mechanism is closed, or, in a case where the fourth opening/closing mechanism is opened, the third opening/closing mechanism is closed; and
    wherein the first fluid sucking section, the second fluid sucking section, and the second fluid discharging section are disposed in positions that are higher than a liquid level in a case where a sample or a buffer solution is stored in the sample storage container, and the sample or the buffer solution contacts the first fluid discharging section.

2. The sample storage apparatus according to claim 1, further comprising a second fluid identification sensor in a position that is outside the sample storage container and that is lower than placement of the second fluid discharging section.

3. The sample storage apparatus according to claim 1, further comprising a second fluid identification sensor for identifying a fluid in the third flow path.

4. The sample storage apparatus according to claim 1, further comprising a second fluid identification sensor for identifying a fluid in a periphery of the first fluid discharging section.

5. The sample storage apparatus according to claim 1, the at least one fluid discharging unit comprising a tube pump or piezoelectric pump.

6. The sample storage apparatus according to claim 1, further comprising a fifth flow path in which downstream portions of the third and fourth flow paths are combined and integrated with each other,
    wherein the at least one fluid discharging unit is disposed in the fifth flow path.

7. The sample storage apparatus according to claim 1, further comprising:
    a fifth flow path that branches off from a middle of the first flow path;
    a branching discharging unit that is disposed in the fifth flow path;
    a fifth opening/closing mechanism that is disposed in the fifth flow path; and
    a sixth opening/closing mechanism that is disposed in the first flow path,
    wherein the apparatus operates in a manner that, in a case where the fifth opening/closing mechanism is opened, the sixth opening/closing mechanism is closed, or, in a case where the sixth opening/closing mechanism is opened, the fifth opening/closing mechanism is closed.

8. The sample storage apparatus according to claim 7, further comprising a controller for controlling the first fluid identification sensor, the first opening/closing mechanism, the second opening/closing mechanism, the third opening/closing mechanism, the fourth opening/closing mechanism, the at least one fluid discharging unit, the branching discharging unit, the fifth opening/closing mechanism, and the sixth opening/closing mechanism.

9. The sample storage apparatus according to claim 1, further comprising a controller for controlling the first fluid identification sensor, the first opening/closing mechanism, the second opening/closing mechanism, the third opening/closing mechanism, the fourth opening/closing mechanism, and the at least one fluid discharging unit.

10. The sample storage apparatus according to claim 1, wherein the lid member has an insertion portion into which a sample recovering unit is insertable.

11. The sample storage apparatus according to claim 1, wherein an upstream portion of the first flow path is connected to the sampling section.

12. The sample storage apparatus according to claim 11, wherein the sampling section is disposed in an isolator, and the first flow path is linked with an exterior of the isolator through a liquid delivery port that is disposed in the isolator.

13. The sample storage apparatus according to claim 11, further comprising a sample supplier for supplying a sample to the sampling section.

14. The sample storage apparatus according to claim 11, further comprising:
    a seventh flow path that communicates with the sampling section;

a buffer solution supplier for supplying a buffer solution to the seventh flow path; and an upstream discharging unit that is disposed in the seventh flow path.

15. The sample storage apparatus according to claim 1, wherein the first flow path includes at least one one-way valve that limits movement of a fluid passing through the first flow path to a direction from the sampling section toward the sample storage container.

16. The sample storage apparatus according to claim 1, wherein the first flow path has a sterile connection coupling.

17. The sample storage apparatus according to claim 1, wherein the second fluid sucking section sucks air.

18. The sample storage apparatus according to claim 1, wherein the lid member is made of a flexible material.

19. The sample storage apparatus according to claim 1, wherein the at least one fluid discharging unit is configured to discharge the fluid received from the third flow path and the fourth flow path toward a waste liquid tank.

20. A sample storage apparatus comprising:
a lid member;
a sample storage container that is hermetically closable by the lid member;
a first fluid sucking section that is disposed in a side portion of the sample storage container or in the lid member;
a second fluid sucking section that is disposed in the side portion of the sample storage container or in the lid member;
a first fluid discharging section that is disposed in a bottom portion of the sample storage container;
a second fluid discharging section that is disposed in the side portion of the sample storage container or in the lid member;
a first flow path that is connected to the first fluid sucking section, the first flow path being used for connecting with a sampling section;
a second flow path that is connected to the second fluid sucking section, the second flow path communicating with an exterior of the sample storage container;
a third flow path that is connected to the first fluid discharging section;
a fourth flow path that is connected to the second fluid discharging section;
at least one fluid discharging unit that receives fluid from the third flow path and the fourth flow path;
a first fluid identification sensor for identifying a fluid in the first flow path,
a fifth flow path that branches off from a middle of the first flow path;
a branching discharging unit that is disposed in the fifth flow path;
a fifth opening/closing mechanism that is disposed in the fifth flow path; and
a sixth opening/closing mechanism that is disposed in the first flow path,
wherein the first flow path has a first opening/closing mechanism, the second flow path has a second opening/closing mechanism, the third flow path has a third opening/closing mechanism, the fourth flow path has a fourth opening/closing mechanism,
wherein the apparatus operates in a manner that, in a case where the first opening/closing mechanism is opened, the second opening/closing mechanism is closed, or, in a case where the second opening/closing mechanism is opened, the first opening/closing mechanism is closed, and,
wherein the apparatus operates in a manner that, in a case where the third opening/closing mechanism is opened, the fourth opening/closing mechanism is closed, or, in a case where the fourth opening/closing mechanism is opened, the third opening/closing mechanism is closed;
wherein the apparatus operates in a manner that, in a case where the fifth opening/closing mechanism is opened, the sixth opening/closing mechanism is closed, or, in a case where the sixth opening/closing mechanism is opened, the fifth opening/closing mechanism is closed.

21. The sample storage apparatus according to claim 20, further comprising a controller for controlling the first fluid identification sensor, the first opening/closing mechanism, the second opening/closing mechanism, the third opening/closing mechanism, the fourth opening/closing mechanism, the at least one fluid discharging unit, the branching discharging unit, the fifth opening/closing mechanism, and the sixth opening/closing mechanism.

22. A sample storage apparatus comprising:
a lid member;
a sample storage container that is hermetically closable by the lid member;
a first fluid sucking section that is disposed in a side portion of the sample storage container or in the lid member;
a second fluid sucking section that is disposed in the side portion of the sample storage container or in the lid member;
a first fluid discharging section that is disposed in a bottom portion of the sample storage container;
a second fluid discharging section that is disposed in the side portion of the sample storage container or in the lid member;
a first flow path that is connected to the first fluid sucking section, the first flow path being used for connecting with a sampling section;
a second flow path that is connected to the second fluid sucking section, the second flow path communicating with an exterior of the sample storage container;
a third flow path that is connected to the first fluid discharging section;
a fourth flow path that is connected to the second fluid discharging section;
at least one fluid discharging unit that receives fluid from the third flow path and the fourth flow path; and
a first fluid identification sensor for identifying a fluid in the first flow path,
wherein the first flow path has a first opening/closing mechanism, the second flow path has a second opening/closing mechanism, the third flow path has a third opening/closing mechanism, the fourth flow path has a fourth opening/closing mechanism,
wherein the apparatus operates in a manner that, in a case where the first opening/closing mechanism is opened, the second opening/closing mechanism is closed, or, in a case where the second opening/closing mechanism is opened, the first opening/closing mechanism is closed,
wherein the apparatus operates in a manner that, in a case where the third opening/closing mechanism is opened, the fourth opening/closing mechanism is closed, or, in a case where the fourth opening/closing mechanism is opened, the third opening/closing mechanism is closed;
wherein an upstream portion of the first flow path is connected to the sampling section; and wherein the sampling section is disposed in an isolator, and the first flow path is linked with an exterior of the isolator through a liquid delivery port that is disposed in the isolator.

* * * * *